(12) United States Patent
Hampton et al.

(10) Patent No.: US 8,121,681 B2
(45) Date of Patent: Feb. 21, 2012

(54) COOPERATING DEFIBRILLATORS AND EXTERNAL CHEST COMPRESSION DEVICES

(75) Inventors: David R. Hampton, Woodinville, WA (US); Ronald E. Stickney, Edmonds, WA (US); Richard C. Nova, Kirkland, WA (US); Stephen W. Radons, Snohomish, WA (US); D. Craig Edwards, Fall City, WA (US); Cynthia Jayne, Redmond, WA (US); Joseph L. Sullivan, Kirkland, WA (US); Steven E. Sjoquist, Lynnwood, WA (US)

(73) Assignee: Physio-Control, Inc., Redmond, WA (US)

( * ) Notice: Subject to any disclaimer, the term of this patent is extended or adjusted under 35 U.S.C. 154(b) by 293 days.

(21) Appl. No.: 11/953,665

(22) Filed: Dec. 10, 2007

(65) Prior Publication Data
US 2008/0114406 A1    May 15, 2008

Related U.S. Application Data

(63) Continuation of application No. 10/652,148, filed on Aug. 29, 2003, now Pat. No. 7,308,304.

(60) Provisional application No. 60/447,587, filed on Feb. 14, 2003.

(51) Int. Cl.
*A61N 1/39* (2006.01)
(52) U.S. Cl. .......................................................... 607/5
(58) Field of Classification Search .................. 607/5, 6, 607/8, 142, 32, 60; 128/202.23, 903
See application file for complete search history.

(56) References Cited

U.S. PATENT DOCUMENTS

| | | | |
|---|---|---|---|
| 4,198,963 A | 4/1980 | Barkalow et al. |
| 4,273,114 A | 6/1981 | Barkalow et al. |
| 4,326,507 A | 4/1982 | Barkalow |
| 4,349,015 A | 9/1982 | Alferness |
| 4,361,140 A | 11/1982 | Barkalow |
| 4,397,306 A | 8/1983 | Weisfeldt et al. |
| 4,424,806 A | 1/1984 | Newman et al. |
| 4,570,615 A | 2/1986 | Barkalow |
| 4,610,254 A | 9/1986 | Morgan et al. |
| 4,770,164 A | 9/1988 | Lach et al. |
| 4,819,627 A | 4/1989 | Connors |

(Continued)

FOREIGN PATENT DOCUMENTS
WO    WO 96/28128    9/1996
(Continued)

*Primary Examiner* — Carl H Layno
*Assistant Examiner* — Roland Dinga
(74) *Attorney, Agent, or Firm* — Marger Johnson & McCollom PC

(57) ABSTRACT

Devices, methods, and software implementing those methods for providing communicating external chest compression (ECC) devices and defibrillation (DF) devices, where the ECC and DF devices can be physically separate from each other. Both ECC and DF devices are able to operate autonomously, yet able to communicate with and cooperate with another device when present. Some ECC and DF devices are adapted to be physically and/or electrically coupled to each other. One ECC device includes a backboard, a chest compression member, a communication module, controller, and at least one sensor, electrode lead or electrode. One DF device includes a defibrillator module, a controller, and a communication module that can communicate with the ECC communication module. The communicating ECC and DF devices may deliver ECC, pacing, defibrillation, ventilation, and cooling therapies, and may deliver instructions to human assistants, in a coordinated and cooperative fashion.

19 Claims, 12 Drawing Sheets

U.S. PATENT DOCUMENTS

| | | | |
|---|---|---|---|
| 4,928,674 A * | 5/1990 | Halperin et al. | 601/44 |
| 5,003,982 A | 4/1991 | Halperin | |
| 5,056,505 A | 10/1991 | Warwick et al. | |
| 5,098,369 A | 3/1992 | Heilman et al. | |
| 5,176,135 A | 1/1993 | Fain et al. | |
| 5,184,606 A | 2/1993 | Csorba | |
| 5,217,010 A | 6/1993 | Tsitlik et al. | |
| 5,222,478 A | 6/1993 | Scarberry et al. | |
| 5,243,975 A | 9/1993 | Alferness et al. | |
| 5,257,619 A | 11/1993 | Everete | |
| 5,287,846 A | 2/1994 | Capjon et al. | |
| 5,295,481 A | 3/1994 | Geeham | |
| 5,327,887 A | 7/1994 | Nowakowski | |
| 5,399,148 A | 3/1995 | Waide et al. | |
| 5,474,533 A | 12/1995 | Ward et al. | |
| 5,487,722 A | 1/1996 | Weaver, II et al. | |
| 5,490,820 A | 2/1996 | Schock et al. | |
| 5,549,659 A | 8/1996 | Johansen et al. | |
| 5,557,049 A | 9/1996 | Ratner | |
| 5,564,416 A | 10/1996 | Jones | |
| 5,630,789 A | 5/1997 | Schock et al. | |
| 5,634,886 A | 6/1997 | Bennett | |
| 5,657,751 A | 8/1997 | Karr, Jr. | |
| 5,664,563 A | 9/1997 | Schroeder et al. | |
| 5,716,380 A | 2/1998 | Yerkovich et al. | |
| 5,738,637 A | 4/1998 | Kelly et al. | |
| 5,743,864 A | 4/1998 | Baldwin, II | |
| 5,769,800 A | 6/1998 | Gelfand et al. | |
| 5,772,613 A | 6/1998 | Gelfand et al. | |
| D399,000 S | 9/1998 | Rothman et al. | |
| 5,806,512 A | 9/1998 | Abramov et al. | |
| 5,833,711 A | 11/1998 | Schneider, Sr. | |
| 5,891,062 A | 4/1999 | Schnock et al. | |
| 5,997,488 A | 12/1999 | Gelfand et al. | |
| 6,021,349 A | 2/2000 | Arand et al. | |
| 6,059,750 A | 5/2000 | Fogarty et al. | |
| 6,066,106 A | 5/2000 | Sherman et al. | |
| 6,090,056 A * | 7/2000 | Bystrom et al. | 601/41 |
| 6,125,299 A | 9/2000 | Groenke et al. | |
| 6,141,584 A * | 10/2000 | Rockwell et al. | 607/5 |
| 6,142,962 A | 11/2000 | Mollenauer et al. | |
| 6,149,670 A * | 11/2000 | Worthen et al. | 607/3 |
| 6,171,267 B1 | 1/2001 | Baldwin, II | |
| 6,174,295 B1 | 1/2001 | Cantrell et al. | |
| 6,179,793 B1 | 1/2001 | Rothman et al. | |
| 6,213,960 B1 * | 4/2001 | Sherman et al. | 601/41 |
| 6,234,984 B1 | 5/2001 | Kelley et al. | |
| 6,259,949 B1 * | 7/2001 | Rosborough et al. | 607/14 |
| 6,263,238 B1 | 7/2001 | Brewer et al. | |
| 6,325,771 B1 | 12/2001 | Kelley et al. | |
| 6,351,671 B1 | 2/2002 | Myklebust et al. | |
| 6,374,827 B1 | 4/2002 | Bowden et al. | |
| 6,390,996 B1 | 5/2002 | Halperin et al. | |
| 6,398,744 B2 | 6/2002 | Bystrom et al. | |
| 6,398,745 B1 | 6/2002 | Sherman et al. | |
| 6,447,465 B1 | 9/2002 | Sherman et al. | |
| 2001/0011159 A1 | 8/2001 | Cantrell et al. | |
| 2001/0018562 A1 | 8/2001 | Sherman et al. | |
| 2001/0025151 A1 | 9/2001 | Kimball et al. | |
| 2001/0047140 A1 * | 11/2001 | Freeman | 601/41 |
| 2002/0007132 A1 | 1/2002 | Rothman et al. | |
| 2002/0026131 A1 | 2/2002 | Halperin | |
| 2002/0026229 A1 | 2/2002 | Weil et al. | |
| 2002/0032383 A1 | 3/2002 | Weil et al. | |
| 2002/0055694 A1 | 5/2002 | Halperin et al. | |
| 2002/0117173 A1 | 8/2002 | Lynn et al. | |
| 2002/0128571 A1 | 9/2002 | Brenneman | |
| 2002/0133197 A1 | 9/2002 | Snyder et al. | |
| 2002/0177793 A1 * | 11/2002 | Sherman et al. | 601/41 |
| 2004/0158303 A1 * | 8/2004 | Lennox et al. | 607/109 |

FOREIGN PATENT DOCUMENTS

| | | |
|---|---|---|
| WO | WO 96/28129 | 9/1996 |
| WO | WO 99/36028 | 7/1999 |
| WO | WO 00/27336 | 5/2000 |
| WO | WO 00/27464 | 5/2000 |

* cited by examiner

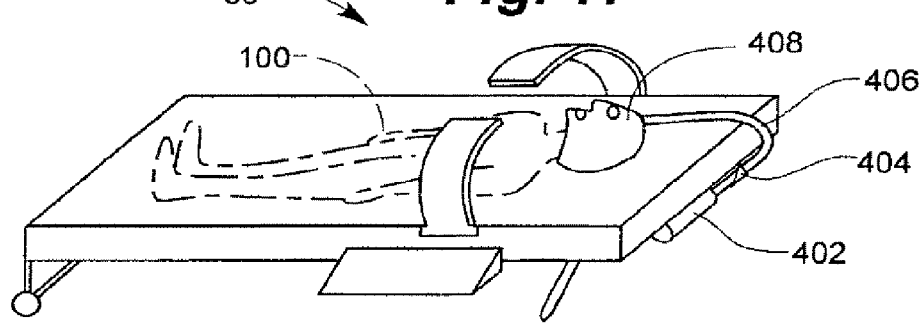
Fig. 17
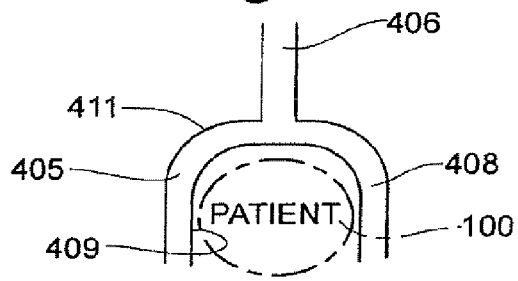
Fig. 18
Fig. 19
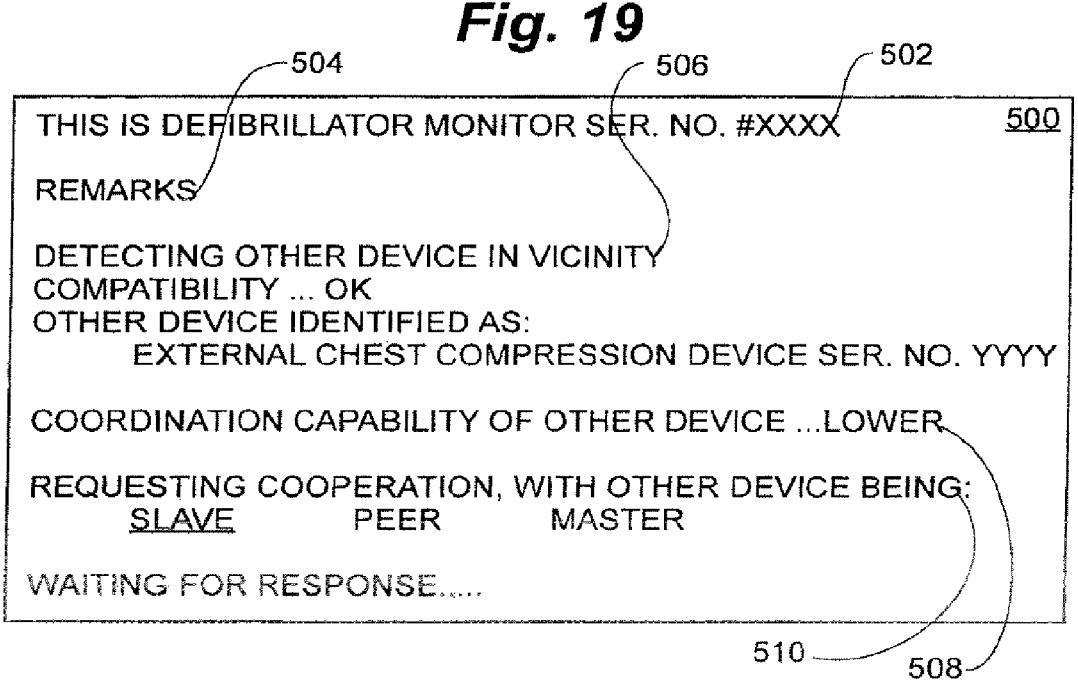

COOPERATING DEFIBRILLATORS AND EXTERNAL CHEST COMPRESSION DEVICES

RELATED APPLICATIONS

This application is a continuation of U.S. patent application Ser. No. 10/652,148, filed on Aug. 29, 2003, and issued as U.S. Pat. No. 7,308,304 on Dec. 11, 2007, and which claims the benefit of U.S. Provisional Patent Application No. 60/447,587, filed Feb. 14, 2003, titled COOPERATING DEFBRILLATORS AND CPR DEVICES. The entire contents of these applications are hereby incorporated by reference in their entirety. The present application is related to U.S. patent application Ser. No. 10/652,392, titled INTEGRATED EXTERNAL CHEST COMPRESSION AND DEFIBRILLATION DEVICES AND METHODS OF OPERATION, and to U.S. patent application Ser. No. 10/652,965, titled DEFIBRILLATORS LEARNINGS OF OTHER CONCURRENT THERAPY, both filed on Aug. 29, 2003.

BACKGROUND OF THE INVENTION

1. Field of the Invention

The present invention is related to the field of resuscitation devices.

2. Description of the Related Art

All over the world, people experience resuscitation events. For example, both in and out of the hospital, there is a significant incidence of cardiac and/or respiratory arrest among at-risk patients. When an acute event occurs, a variety of therapies may need to be administered to restore the patient's normal function. The patient may require artificial respiration to stimulate breathing, chest compressions to restore perfusion, defibrillation to activate the heart, and/or pacing to promote cardiac output.

Many devices exist which can separately administer these therapies in these events and situations. For example, an automated chest compression device is taught in patent U.S. Pat. No. 6,234,984 B1. Some of these devices even aggregate various features, such as are described in U.S. Pat. Nos. 4,349,015, and 4,424,806.

Many of the prior art devices, however, merely collect such features into a single package, without synchronizing their functions and making them work together. Therefore there exists a need for devices that can combine, coordinate and integrate various aspects of these diagnostics and therapies to better assess and treat the patient. That is because many of these conditions occur in combination, requiring that therapies blend constructively with one another to be optimally effective.

SUMMARY OF THE INVENTION

Generally, the present invention provides devices, software, and methods as described below. The invention offers devices that can operate independently, or in a combined fashion, to monitor a patient and administer diverse therapies, as they arise. Systems provided by the present invention preferably include a device for providing external chest compression and a defibrillator, where the chest compression device and defibrillator can each operate autonomously when necessary, yet can also each communicate with and cooperate with each other when advantageous.

One system provided by the present invention includes an external chest compression (ECC) device having a first communication module, and a defibrillator having a second communication module, in which the ECC device and the defibrillator are capable of communicating via the first communication module and the second communication module. The data communication modules can utilize a communications medium selected from the group consisting of wireless, radio frequency, infra-red light, light, hard-wired electrical, and coupled optical fibers.

Some ECC devices include a backboard, and can also include wheels and a handle. A chest compression member can be coupled to the backboard, where the chest compression member can include a rigid chest compression member and/or a retractable or contractible belt or vest. Some chest compression members are driven by powered actuators while others are manually operable. ECC devices can also include cooling modules for cooling a person and ventilators for ventilating.

ECC devices, on the backboard, on the chest compression members, and/or on the defibrillation device, can include various sensors, electrodes, and leads, which can include sensors for measuring physiological attributes, one or more defibrillation electrodes, and one or more EGG leads. Electrodes may include a releasable electrolyte. Sensors can measure applied chest pressure, temperature, respiration, pulse, ECC signals, EEG activity, thoracic impedance, and other parameters. The sensors, electrodes, and leads are preferably coupled to the communication module of the respective ECC or defibrillation device. Some systems include a communication module on either or both of the ECC device and defibrillator that can communicate with a remote assistance center. A camera can be coupled to the communication module.

Some ECC devices and defibrillators are adapted to be physically and/or electrically coupled to each other. Some defibrillators can be electrically coupled to defibrillation electrodes on the ECC device.

The ECC device and/or the defibrillator preferably includes a controller or processor that is coupled to the respective bidirectional communication module. In systems having at least two controllers, each controller may execute logic to designate a master controller, and also slave controllers, as between the two or more controllers. Various methods may be executed in the controllers, including the master and/or slave controllers, depending on the embodiment.

One method according to the present invention includes placing a person on a first device, establishing data communication between the first device and a second device that can be physically apart from the first device, causing a chest compression member of the first device to compress the chest of the person against the backboard, and causing a defibrillator of the second device to defibrillate the person responsive to the communication. Placing the person on the first device can refer to placing the person on a portion of the first device, for example on a backboard, or on a vest or belt which encircles the person. Some embodiments utilize a constrictive vest or belt and do not include a backboard or backframe. The communication may be used either to synchronize the delivery of the defibrillator shock with an optimal time in the compression cycle, or to avoid applying the defibrillator shock at a vulnerable period in the compression cycle. The communication about defibrillator activity may, in turn, be used to initiate, pause, or terminate chest compressions, or to change operating parameters of the ECC device, such as rate and/or depth of chest compression. In some methods, placing the person on a backboard of the first device results in the person contacting a defibrillator electrode of the first device.

Some methods include therapies, including pacing, ventilating, cooling, and other modalities, and providing ECC responsive to data communicated between or among the separate devices. The therapies performed on the person can be automatic, manual, or prompted manual mode, in response to voice instructions from any of the devices.

Some systems include a controller executing logic for generating an output to control a chest compression actuator in combination with a defibrillator, responsive to sensor data indicative of the presence of cardiac arrest and that indicate the response of the patient to therapy. In one example, a sensor may detect that a patient is in cardiac arrest (for example, some combination of asystole or VF on the ECG, lack of a pulse, and no respiratory and/or EEG signal) or pulseless electrical activity (PEA) (for example, some combination of R-wave activity on the ECG and lack of a pulse). Alternatively, the sensor may detect that the patient has a perfusing rhythm, such as sinus activity (for example, R-wave activity, a regular pulse, and adequate respiration.)

Perfusion may be stimulated when controllers execute logic in response to sensor inputs to implement methods to administer automatic chest compressions, as in cardiac arrest or PEA. Further sensor readings can establish whether adequate perfusion has been stimulated, for example, by the return of pulse or EEG signals, and the device may recommend or self-adjust based on sensor readings to set an optimal rate and/or depth of chest compression. Some indication of the adequacy of perfusion and the course of ECC therapy can be indicated to the operator and stored to a documentation log.

Similarly, it may be determined that defibrillation is required in order to restore spontaneous cardiac contractions and to restore cardiac output. Sensors may initiate defibrillation responsive to physiological signals indicative of ventricular fibrillation or ventricular tachycardia. A defibrillation shock can be administered under manual or automatic control, synchronized to the activity of the ECC device, and the response of the patient can be determined by further reference to the sensors (e.g. pulse or ECC).

Again, sensors may indicate that a patient is failing to ventilate properly, or only with difficulty. Manual or automatic ventilation may be initiated in conjunction with, and the effectiveness determined by reference to sensors (e.g. $CO_2$ or oximetry). Optimal rate and depth, or possibly gas mixture, may be determined and recommendations made to the operator. The interaction between sensors and therapies may again be used to establish a care record in a documentation log. Similarly, other adjunct therapies (hypothermia and others) may be applied when the sensors indicate that their effect is beneficial and safe for the patient. ECC may be started, paused, or stopped in relation to these adjunct therapies.

Each independent therapies may be applied alone or in combination. But a patient in cardiac arrest may benefit most from a synchronized combination of therapies, based on sensor readings. This could occur when a patient has been placed on an ECC device and instructions generated to establish communication between a first data communication module operably coupled to the ECC device and a second data communication module coupled to a defibrillator. Sensors may determine that a patient is in cardiac arrest, and, for example, may further indicate that the patient has been in a non-perfusing state for a period longer than 5 minutes. The device would recognize that a period of chest compressions should be initiated, sufficient to perfuse the patient, for two minutes before applying a defibrillation shock. The effectiveness of chest compression could be monitored, and the duration of stimulated perfusion measured. After two minutes, a defibrillation shock could be automatically applied. It may be desirable to initiate the shock during a chest compression, or between them, with such synchronization being performed to enhance shock effectiveness. Sensors detecting the reappearance of a perfusing ECG rhythm may initiate a 30-second period of pacing to further stimulate cardiac function. Alternatively, failure to restore a perfusing rhythm may cause a further period of CPR, followed by another defibrillation shock, to be administered. In all cases available therapies can be synchronized and combined in ways responsive to the patient's condition, and in ways that complement each other's effectiveness.

Figure 1:
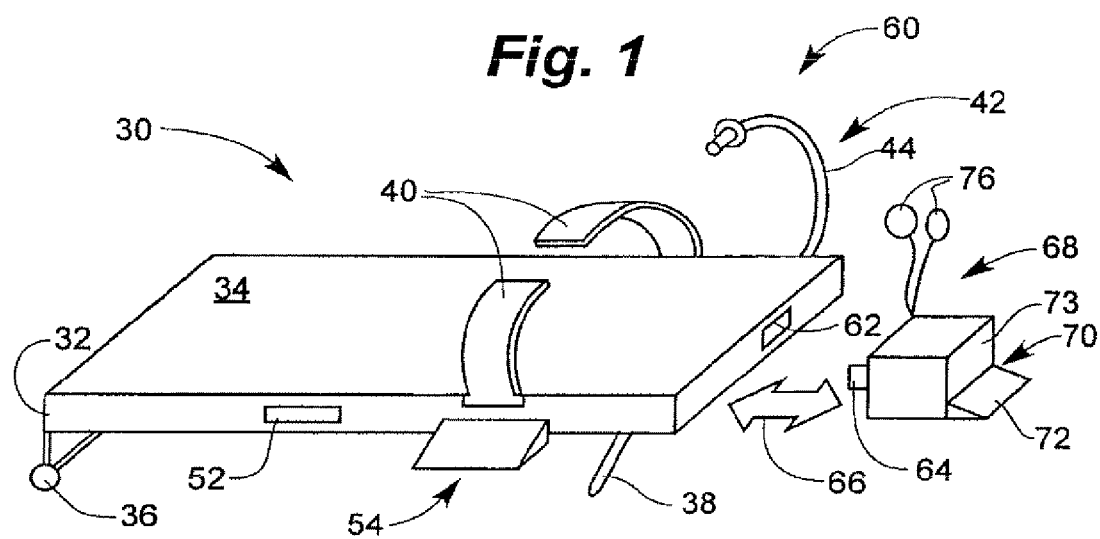
FIG. 1 is a perspective view of a system including a cooperating, communicating, and physically separate external chest compression (ECC) device and defibrillation device.
Figure 10:
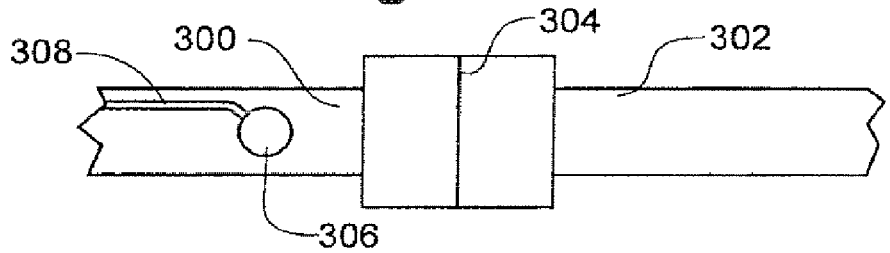
Figure 11:
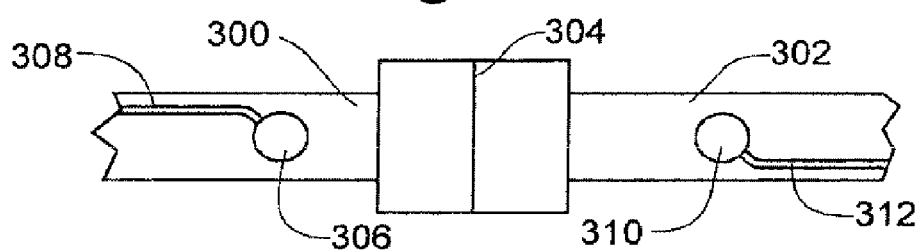
Figure 12:
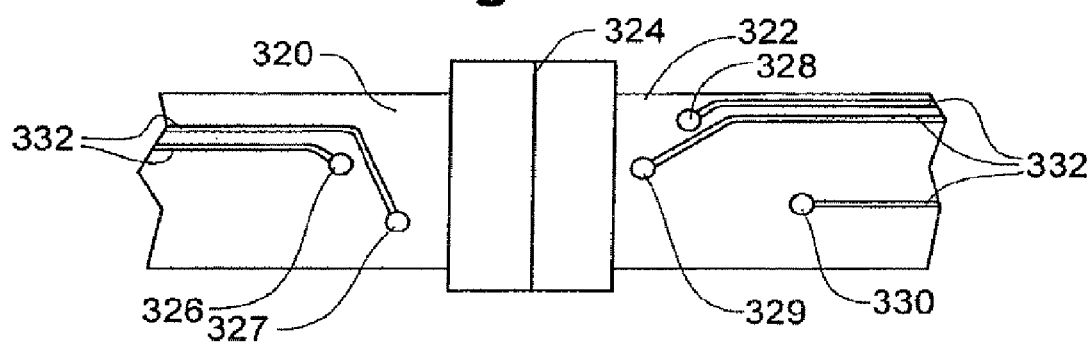
Figure 13:
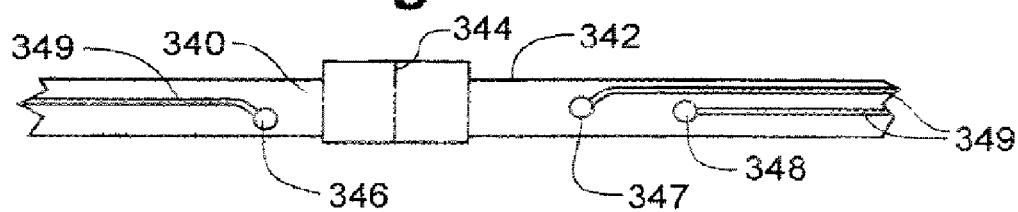
Figure 14:
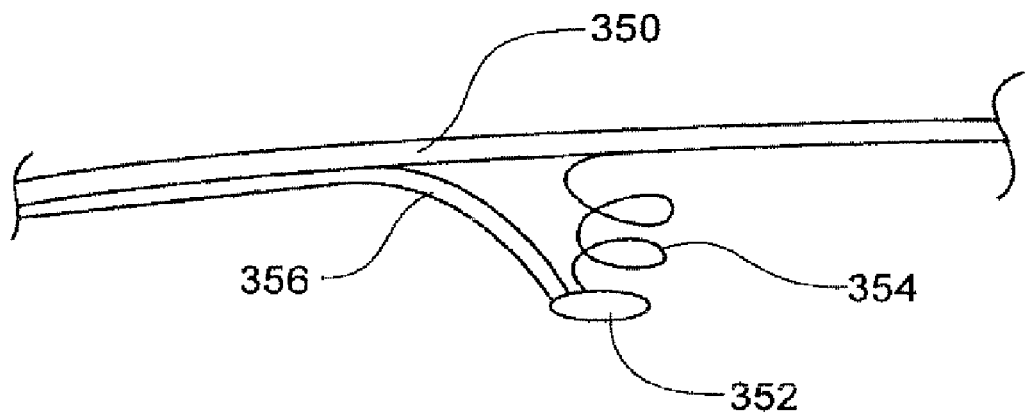
Figure 15:
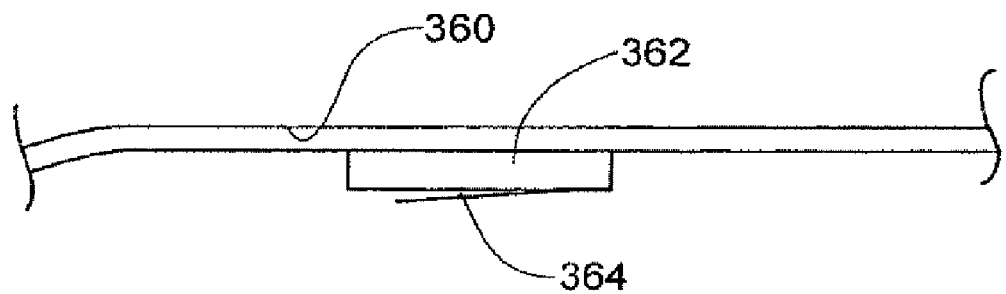
Figure 16:
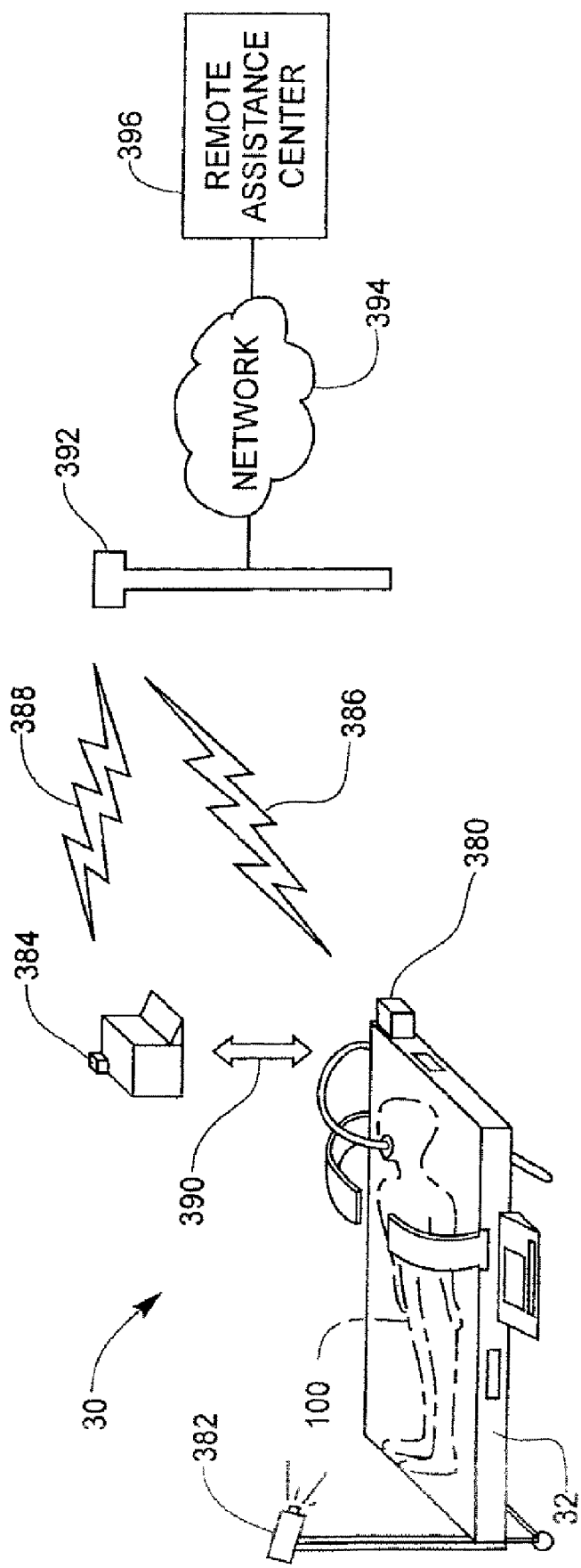
Figure 20:
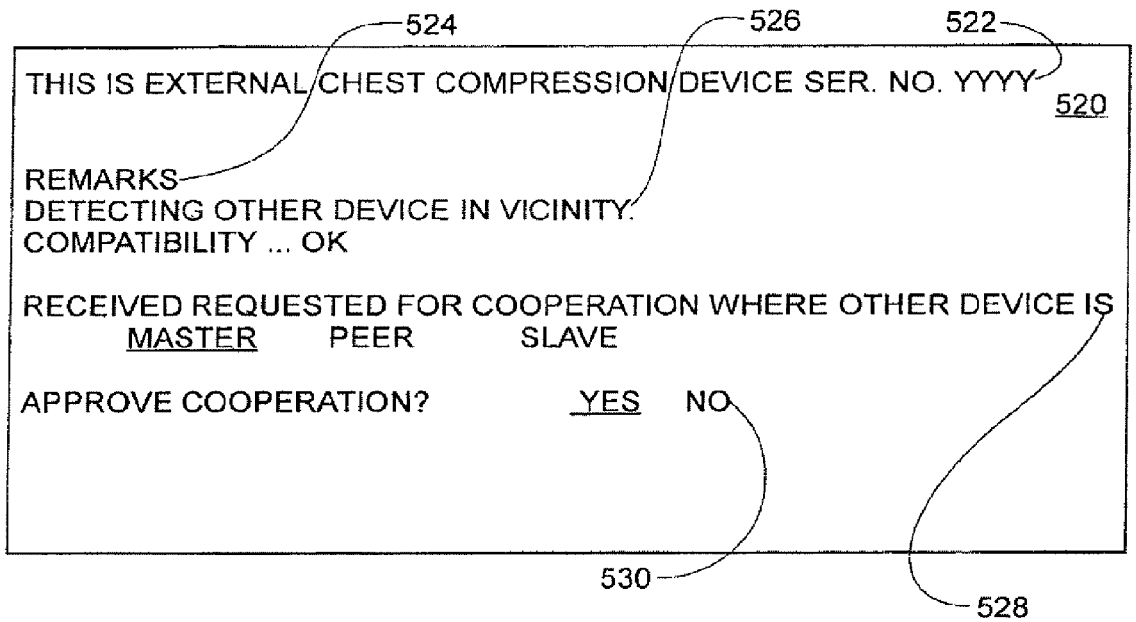
Figure 21:
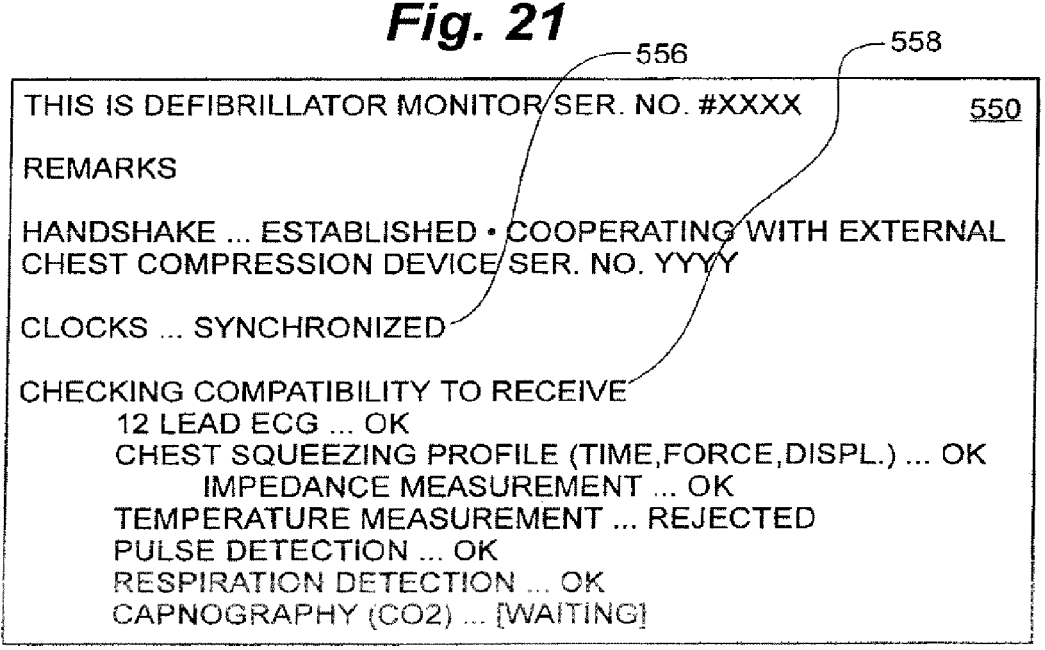
Figure 22:
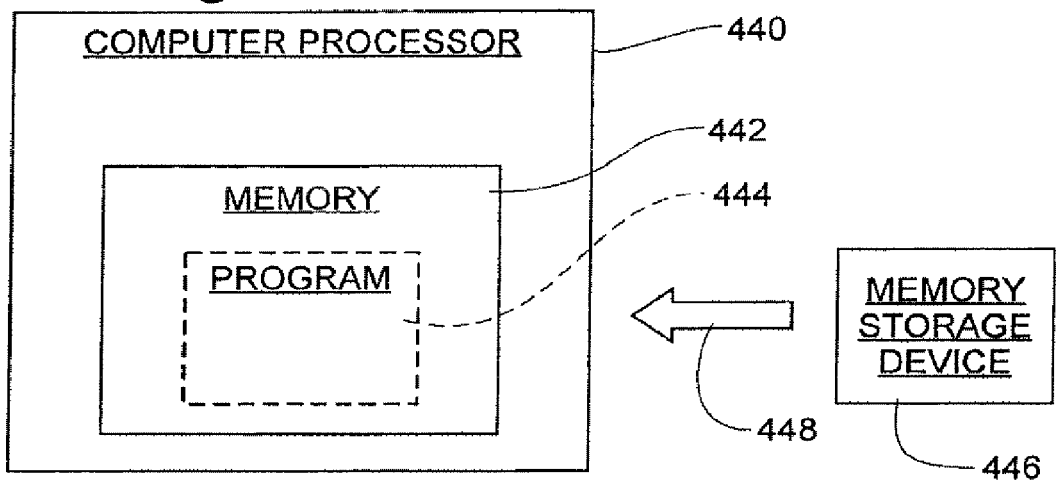
Figure 23:
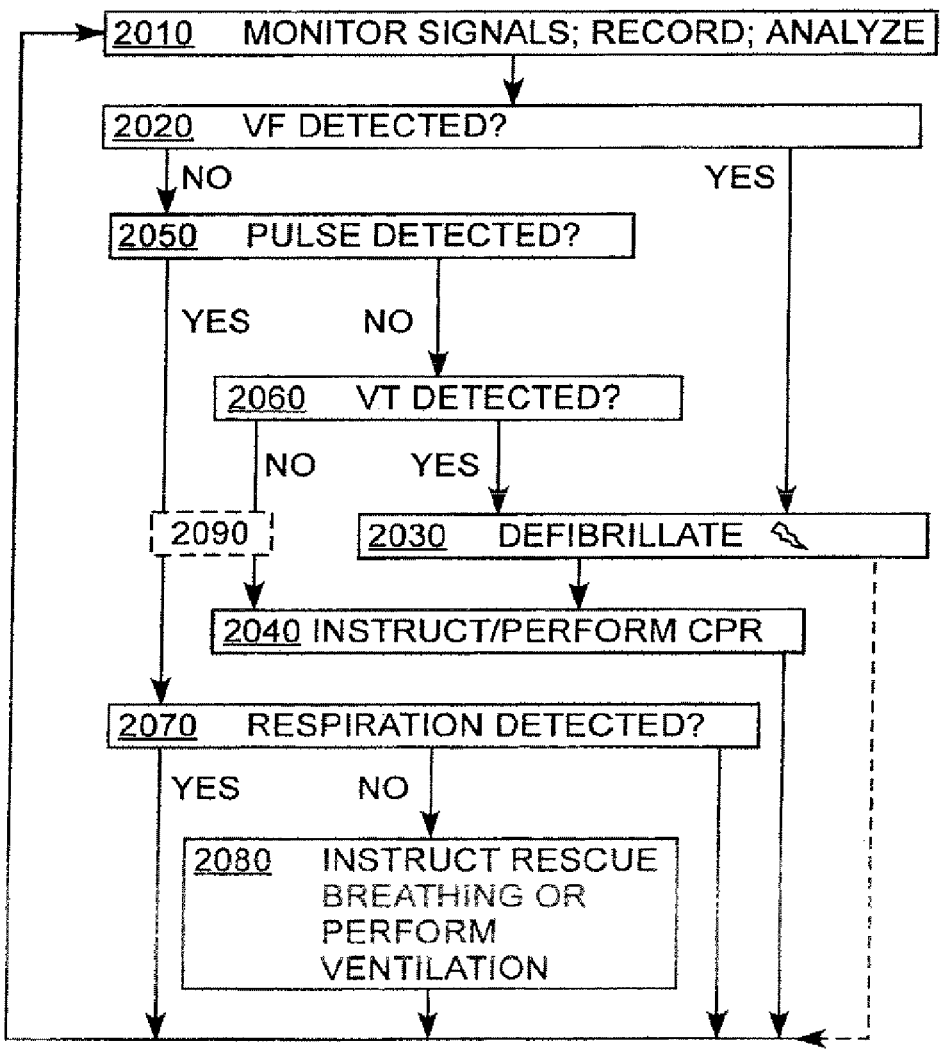
Figure 24:
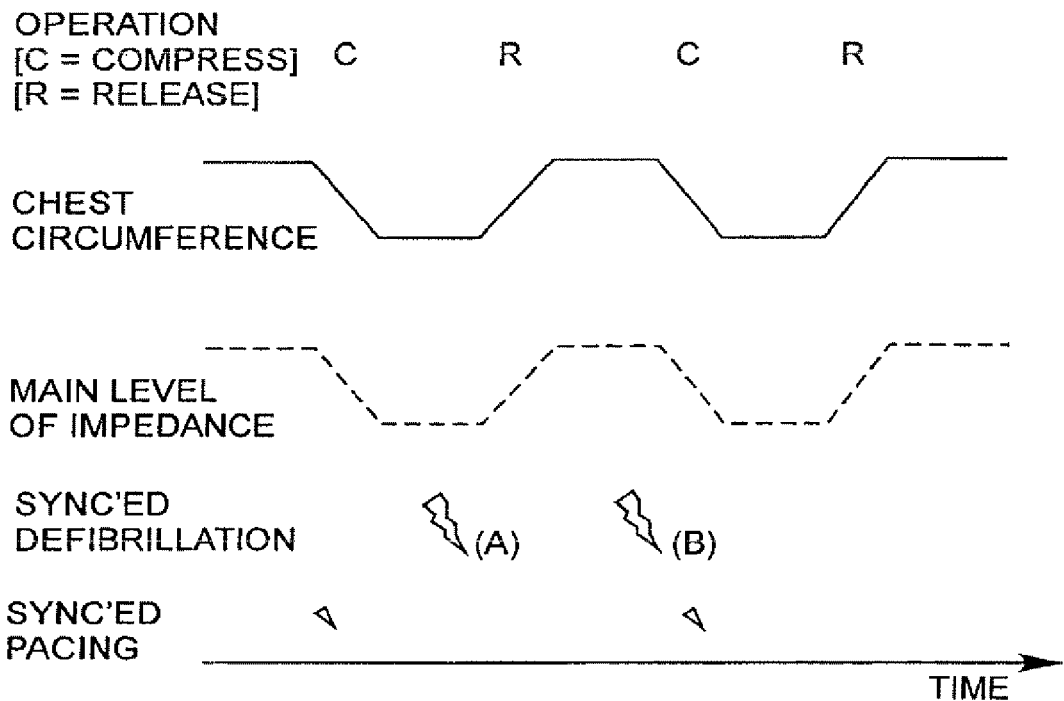
Figure 25:
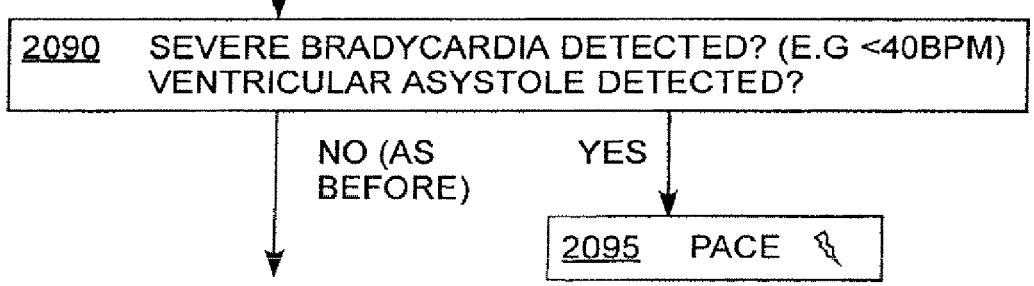
Figure 26:
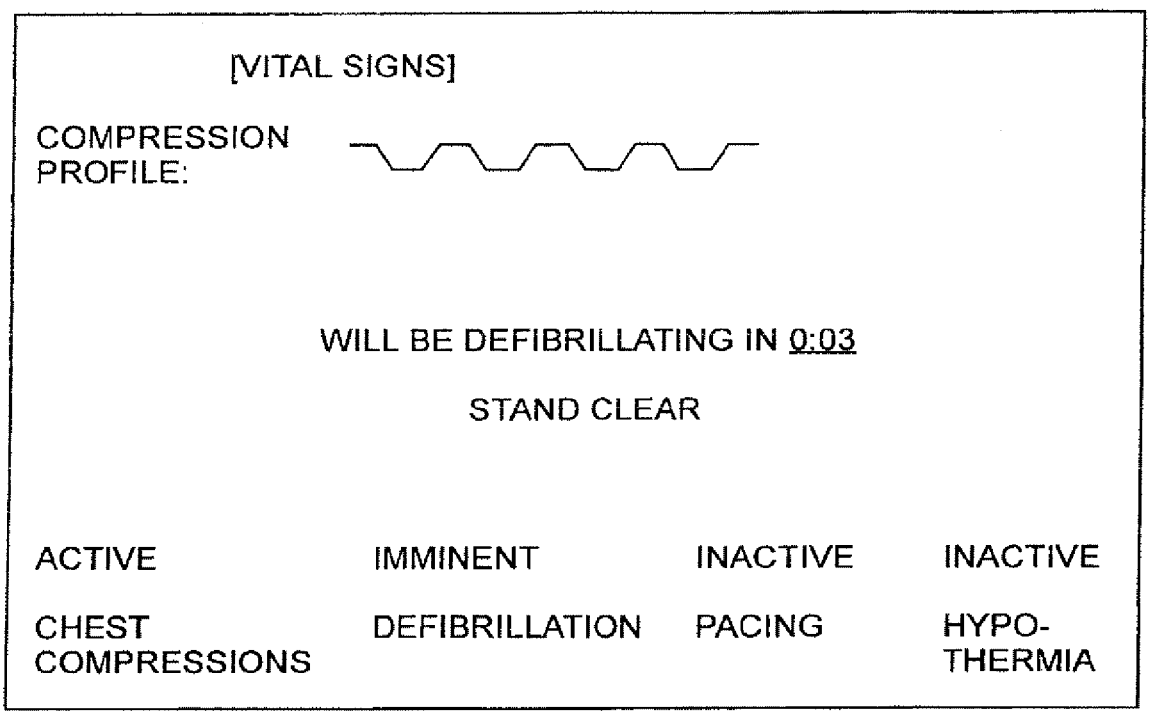

cooperating external chest compression (ECC) device and a separate defibrillation device, in which the ECC device includes electrodes for receiving defibrillator paddle electrodes for electrically coupling to the defibrillation device;

FIG. 10 is a fragmentary, bottom view of a belt bearing a defibrillator electrode;

FIG. 11 is a fragmentary, bottom view of a belt bearing two defibrillator electrodes;

FIG. 12 is a fragmentary, bottom view of a belt bearing multiple ECG leads;

FIG. 13 is a fragmentary, bottom view of a belt bearing multiple sensors and associated leads;

FIG. 14 is a fragmentary, transverse cross-sectional view of a belt or vest bearing a spring biased defibrillator electrode, ECC lead, or sensor;

FIG. 15 is a fragmentary, transverse cross-sectional view of a belt or vest bearing an electrode, lead, or sensor having an electrolyte gel;

FIG. 16 is a schematic view of an ECC device and defibrillator similar to those FIG. 1, further including communication modules in communication with a camera and transmitter communicating with a remote assistance center;

FIG. 17 is a schematic view of the ECC device of FIG. 1, further including a cooling module in the form of a cooling garment disposed on the person;

FIG. 18 is a highly diagrammatic, cross-sectional view of the person and cooling garment of FIG. 17;

FIG. 19 is a view of a sample screen of a defibrillator according to the invention, when it requests cooperation with an ECC device according to the invention;

FIG. 20 is a view of a sample screen of the ECC device of FIG. 19, when the request is received;

FIG. 21 is a view of a sample screen of the defibrillator of FIG. 19, as the handshake is being established;

FIG. 22 is a block diagram of the controller or computer containing executable logic or software contained within an ECC and/or defibrillation device;

FIG. 23 is a flow chart illustrating a method for performing coordinated external chest compression and defibrillation therapies;

FIG. 24 is a time diagram showing coordinated periodic chest compressions and defibrillation and/or pacing pulses;

FIG. 25 is a flow chart segment illustrating an optional pacing portion of the flow chart of FIG. 18; and FIG. 26 is a view of a display screen from an operation of the invention.

DETAILED DESCRIPTION

According to the invention, an external chest compression (ECC) device is provided, and also an external defibrillator. In addition, each has an interface for communicating with the other, and optionally also for cooperating for maximum effect. The interfaces are made compatible with each other, as further described below.

An important aspect of the invention is that the external defibrillator is capable of functioning autonomously, independently of the external chest compression device when they are not communicating or cooperating. It is also highly preferable that the external chest compression device be capable of functioning autonomously, independently of the external defibrillator when they are not communicating or cooperating.

FIG. 1 illustrates a system 60 for performing coordinated ECC and defibrillation including an external chest compression (ECC) device 30 and an external defibrillation device 68. ECC device 30 includes a backboard or back frame 32, chest compression members 40, a ventilator 42, an ECC human interface module or I/O module 54, and a communication module 62 for communicating with external defibrillation device 68.

Backboard 32 is shown as solid and having an upper surface 34. Backboard 32 need not be solid. Backboard 32 is preferably made as lightweight as possible, allowing the integrated modules to be included without adding unneeded weight. In some embodiments, wheels 36 and a handle 38 are coupled to backboard 32. This permits the device to be used as a gurney, making it easier to transport the patient.

The chest compression portion may be implemented in a number of ways, as described below. Two chest compression members 40 are shown, in the form of two arms. Chest compression members 40 are coupled to backboard 32. Even though only two arms are shown, the chest compression members may be implemented as a belt, and/or as a vest, either a full or partial vest. The belt or vest is intended to generally wrap around the chest of the patient, for squeezing it, or squeezing it against backboard 32. In this way, ECC or CPR can be administered to the patient. The belt or vest may incorporate other functionalities, as further described below. In addition, it may be removable and/or reusable.

ECC device 30 can further include ventilator or ventilating module 42. Ventilator 42 can include ventilator tubing 44. Ventilator 42 can also be coupled to backboard 32 and can be used for ventilating the patient. Ventilator 42 is shown schematically, as ventilators are well known to those skilled in the art.

Human interface module 54 can be implemented in a number of ways. Human interface module 54 can include an input portion and an output portion. The input portion can include a keyboard and the output portion can include a visual display or computer screen and/or a voice output module for interacting with a human assistant. Human interface module 54 can have input devices such as keys, switches, knobs, levers, and a microphone for recording and preferably also voice recognition. The human interface device can also have output devices such as one or more display screens, a speaker, a printer, and other output devices. All of these functions may be aggregated at the human interface module, for example, using a keypad.

In addition, the ECC device may include advanced features for availing to a defibrillator, when one is coupled with it. This may be useful when the defibrillator is a unit that lacks many capabilities on its own. Having these features permits using a defibrillator that itself lacks these features.

A battery 52 can be carried within backboard 32 for supplying power for operating human interface device 54, ventilator 42, and chest compression members 40, in the various embodiments of the invention. In some systems, battery 52 can also be used to power the external defibrillator, where the defibrillator can be electrically coupled to the ECC device. A controller or computer can also be included within human interface device 54 or elsewhere within ECC device 30 for coordinating the operation of external chest compression, defibrillating, pacing, and ventilating, depending on the embodiment of the invention present.

External defibrillation device 68 includes a defibrillation human interface 70 including an input portion 72 and an output portion 73. The input portion can include a keyboard and the output portion can include a visual display or computer screen and/or a voice output module for interacting with a human assistant. Defibrillation device 68 also includes defibrillation electrodes 76 and a defibrillation communication module 64. Defibrillation communication module 64 may be seen communicating with ECC device communication module 62 through communication channel 66.

Figure 2:
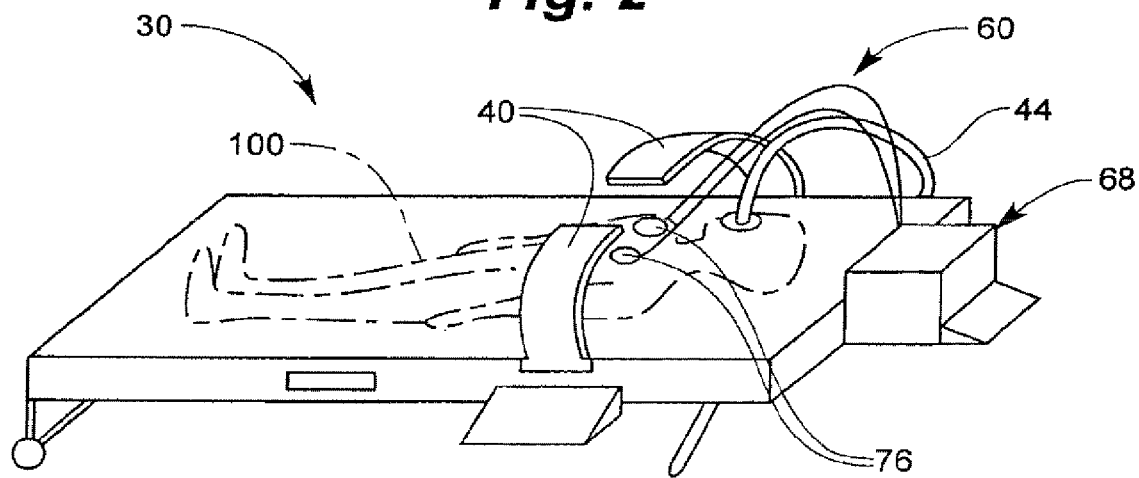
FIG. 2 is a perspective view of the system of FIG. 1, having a person disposed on the ECC device, and the ECC and defibrillation devices directly coupled to each other.

FIG. 2 illustrates system ECC device 30 having a person or patient 100 disposed on backboard 32. Patient 100 has a chest disposed under chest compression members 40 and a mouth for receiving ventilator tubing 44. Defibrillator device 68 has been moved toward ECC device 30. In some embodiments, ECC device and defibrillator device 68 can be electrically and/or mechanically coupled to each other through electrical connectors and/or cables, allowing defibrillation pulses from the defibrillator to be delivered through defibrillation electrodes of the ECC device.

Figure 3:
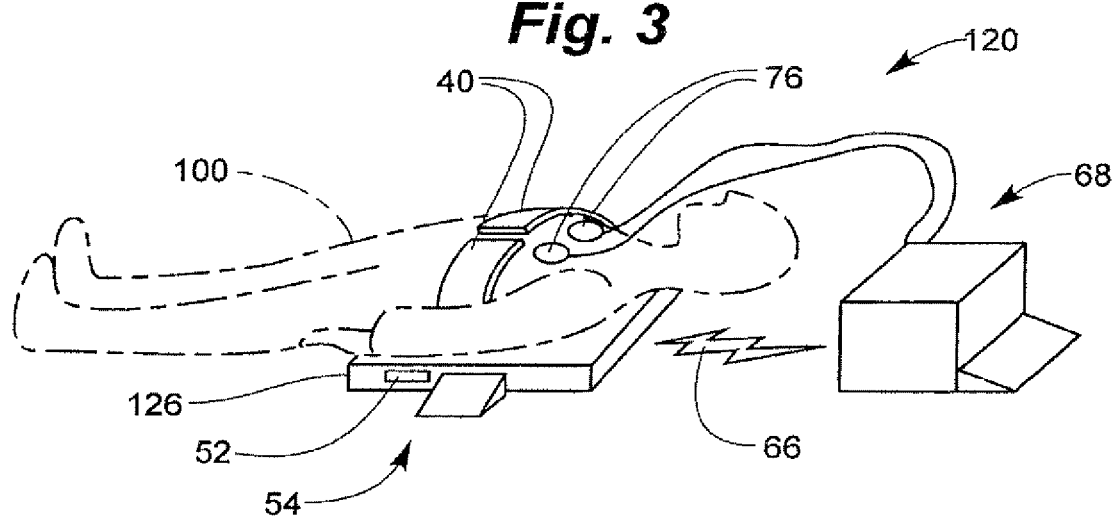
FIG. 3 is a perspective view of a person disposed on another system ECC device having a shorter backboard relative to the ECC device of FIG. 1, and having the defibrillation electrodes on the person.

FIG. 3 illustrates another system including an ECC device 120, for providing cooperating external chest compression and defibrillation and/or pacing. ECC device 120 may be seen to include chest compression members 40, human interface device 54 and battery 52, as previously described with respect to FIG. 1. FCC device 120 includes a short backboard or back frame 126. Shorter backboard 126 can decrease the weight and increase the portability of the ECC device.

Compressing and releasing may be performed according to any type of time profile. One such profile is seen in FIG. 24. Other profiles may be sine wave, triangular shaped, or other shapes. In an advantageous embodiment of the invention, a sine wave may be used with a frequency outside the ECG range. The chest compression profile shape and frequency may permit analyzing the ECG while simultaneously performing chest compressions. This may also permit the device to detect more quickly a rhythm that requires a defibrillation shock, and to reduce the delay of its delivery from the end of the chest compressions.

Other embodiments of the chest compression portion includes devices performing active compression decompression, devices that combine chest compressions with abdominal compressions, devices where the belt is operated electronically (w/o gears), and devices that use electricity to do chest compressions by electrically inducing chest muscles to contract.

Referring again to FIGS. 1, 2, and 3, the invention external defibrillation device is capable of performing defibrillation, and optionally, also pacing. Pacing may be implemented by a separate module than defibrillating, but it is highly advantageous to have the same module perform both functions. The defibrillator may be of any chosen automation level. That includes operation that is fully automated to fully manual, and every option in between.

Moreover, the defibrillator may also advantageously provide devices or modules that perform monitoring, and further provide interpretation of the monitored signals. The monitoring results may advantageously be displayed on the human interface device previously described or on an I/O module as described below. In other embodiments, there is a separate monitoring module. Monitoring may be of any of the monitoring parameters or physiological attributes common on defibrillator/monitors or bedside monitors today, for example, NIBP, $SPO_2$, $CO_2$, 12 lead ECG, etc. In other embodiments, monitoring is performed by the ECC device, and may be transmitted to the defibrillator.

The defibrillator also can include an input/output (I/O) or human interface module as previously described. In the embodiment of FIG. 1, defibrillator human interface device 70 includes a display screen and keyboard, as previously discussed, but that is not limiting. The invention can also have input devices such as keys, switches, knobs, levers, a microphone for voice recording, and preferably also voice recognition, and output devices such as one or more screens, a speaker, printer, or other output device. All of these are preferably aggregated at the I/O module, but that is not necessary for practicing the invention. They may be located elsewhere in the devices, or received remotely, for example, wirelessly.

The ECC device also optionally includes a ventilation portion. A ventilation portion or ventilating module 42 was previously described with respect to FIG. 1. The ventilation portion may be implemented either automatically, or be intended for use by a human operator. If by a human, the device may be made giving prompts for instructing the rescuer. The prompts may be timed. The rescuer may be either performing mouth-to-mouth resuscitation or opening a bag valve mask device where the user manually squeezes the bag. If the ventilator is to be automatic, a tube can be inserted into the patient's mouth, and a pump can be used. A mask may be placed on the face of the patient. The oxygen can be delivered this way to the patient. Other devices, such as valves that block the airway during chest decompression, for example, a CPR-x valve, can be included in the ventilation portion of the device of the invention.

The ECC device preferably also includes an electrical power source for powering the various ECC portions. The power source may be a battery, such as battery 52 discussed with respect to FIG. 1. The battery may be either a rechargeable battery for maximum portability, or a replaceable battery. The battery is preferably integrated with the back frame, either permanently, or in such a way that it can be removed and replaced. Some devices of the invention have the benefits of being able to share a common power source, CPU or controller, and I/O module for the interface with the rescuer.

Figure 4:
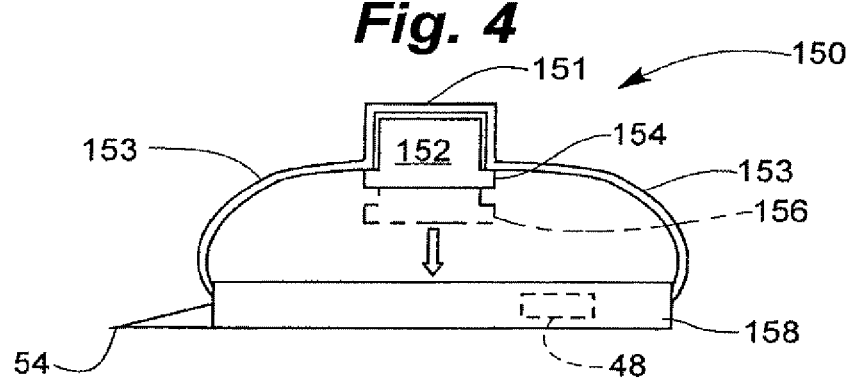
FIG. 4 is a transverse, cross-sectional view of an ECC device in which the chest compression member includes a belt and a piston.

FIG. 4 illustrates an ECC device 150, in which the chest compression is effected by a compressor or expandable member held in place by a belt or vest 153, depending on what is provided in the particular embodiment. The chest compressor includes a mechanism for pushing downwards on the chest. In the ECC device illustrated, the compressor is implemented as a base 151 and a piston 152. Piston 152 is illustrated in a first, retracted position 154 and a second, extended position 156. Belt or vest 153 can be coupled to a back frame 158, as previously discussed. A posterior electrode 48 is embedded in the back frame 158.

Figure 5:
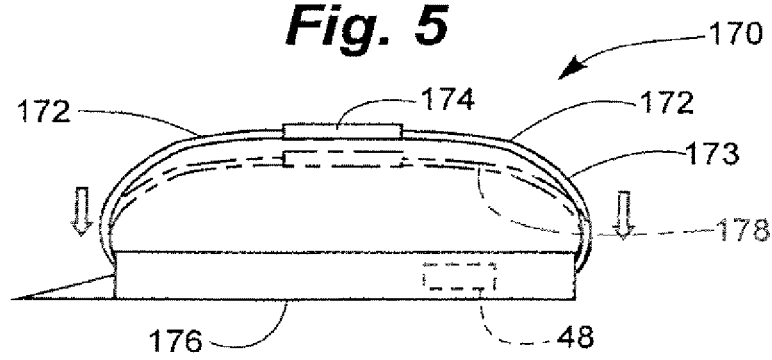
FIG. 5 is a transverse, cross-sectional view of an ECC device in which the chest compression member includes a retractable belt.

FIG. 5 illustrates an ECC device 170 with a belt or vest 172, having a buckle or zipper 174 for fastening around the chest of the patient. Belt or vest 172 can itself be contracted to effect chest compression. The contraction can take place in many ways. In one way, the belt or vest can be retracted into a back frame 176. In another way, belt or vest 172 can be constricted about the patient. Belt or vest 172 may be seen having a first, expanded position 173 and a second, constricted position 178. In yet another way, chest compression is effected by electrically stimulating the chest muscles. A posterior electrode 48 is embedded in the back frame 158.

Figure 6:
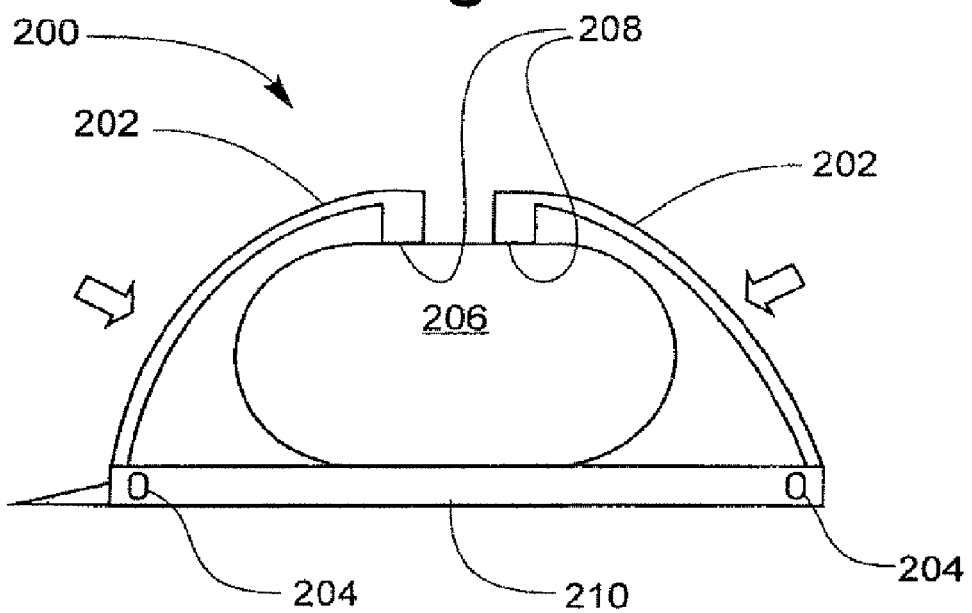
FIG. 6 is a transverse, cross-sectional view of an ECC device in which the chest compression member includes rigid members pivotally coupled to the backboard.

FIG. 6 illustrates still another ECC device 200 having a patient 206 disposed on a backboard 210. In device 200, chest compression is provided by rigid chest compression members or arms 202 having support prongs 208 that push down on the chest of patient 206. Arms 202 can be pivotally coupled to backboard 211. In the embodiment illustrated, arms 202 are operated by gears 204 that are integrated with backboard 210. In some embodiments, arms 202 are driven by a powered chest compression actuator.

Figure 7:
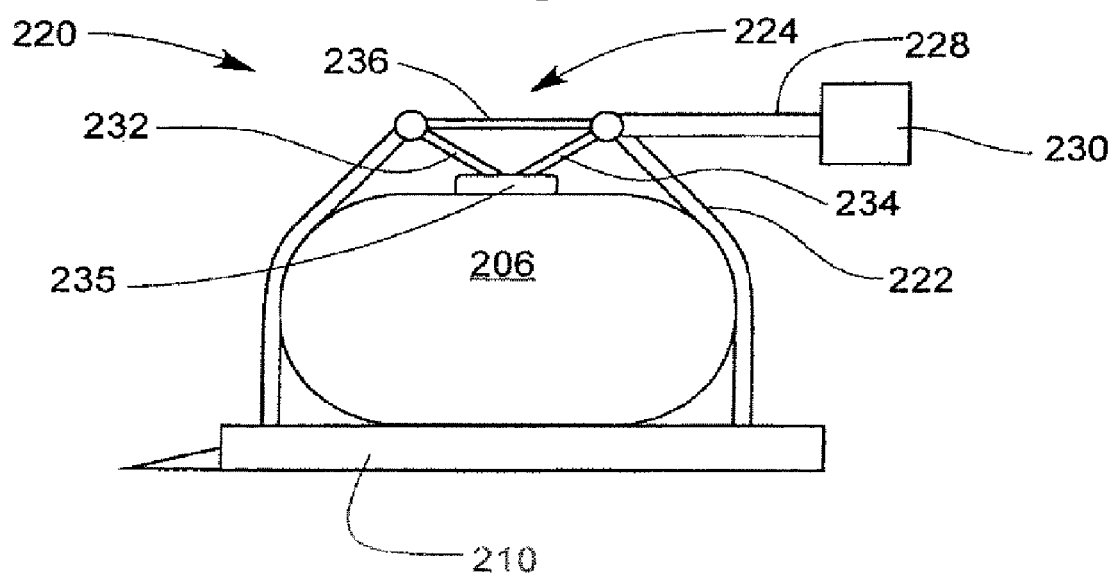
FIG. 7 is a transverse, cross-sectional view of an ECC device having a powered actuator coupled to a force multiplier for delivering chest compression.

FIG. 7 illustrates another ECC device 220 including backboard 210 carrying patient 206, as previously described. ECC device 220 includes a force multiplier 224 using a lever arrangement, so that a pressing member can exert a downward pressure on the patient chest. ECC device 220 includes a gearbox or a powered actuator 230 coupled through a shaft or rod 228 that may be hollow in some embodiments. Shaft 228 can have first force transmission member 236 slidably received within shaft 228 and pivotally coupled to a second force transmission member 232 and a third force transmission member 234. Force transmission members 232 and 234 can be further coupled to a chest compression pad 235 for pressing against the chest of patient 206. Force multiplier device 224 can be held in place by a belt or vest 222. In some embodiments, the lever arrangement may operate by having a rod conduct a long rotation, such as in a corkscrew arrangement.

Other embodiments of the chest compression portion include belts crossing the chest from over the shoulder down to the chest, forming an "X" across the patient's chest. This is better than the conventional way of having belts horizontally across the patient's chest, in that it permits placement of sensors such as leads in different places. Alternately, an "X"-belt configuration may be combined with the conventional configuration. In yet other embodiments, the chest compression portion includes devices performing active compression-decompression, devices that combine chest compressions with abdominal compressions, devices where the belt is operated electronically without gears, and devices that use electricity to do chest compressions by electrically inducing chest muscles to contract. Various embodiments may use combinations of these chest compression techniques.

Figure 8:
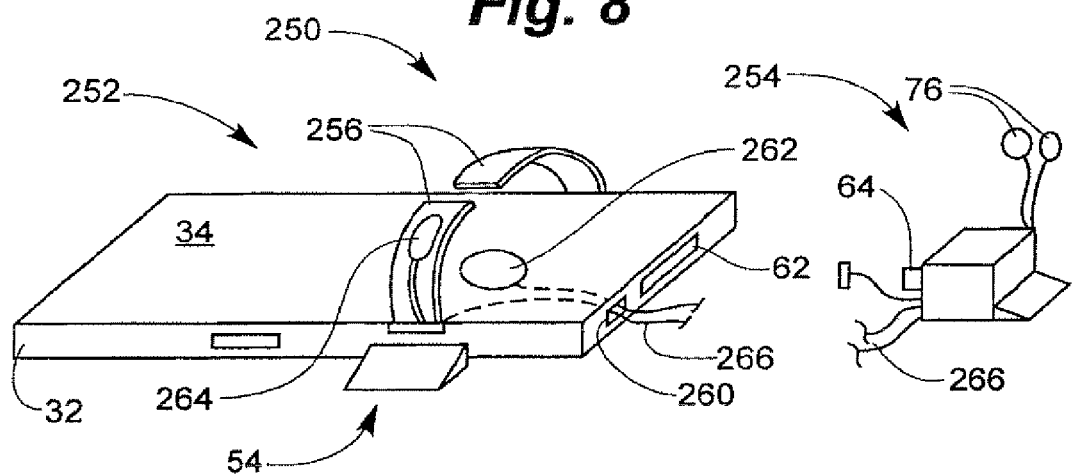
FIG. 8 is a perspective view of a system including a cooperating external chest compression (ECC) device and a separate defibrillation device, in which the ECC device includes a posterior electrode in the backboard and an electrical connection coupled to the defibrillation device.

FIG. 8 illustrates a system 250 including an external chest compression (ECC) device 252 and an external defibrillation device 254. ECC device 252 can have backboard 32, human interface device 54, and ECC data communication module 62, as previously described. ECC device 252 further includes chest compression members 256 having a built in electrode 264 on the underside, and a posterior electrode 262 built into the backboard, for availing to a defibrillator, when one is coupled with it. Electrodes 264 and 262 are placed on the patient by virtue of applying the ECC device. In the example illustrated, one electrode can be integrated with the chest compression portion, and the other on the back frame. In another example, both electrodes may be integrated with the chest compression portion. Instead of applying the external defibrillator electrodes to the patient, special wires can be applied from the external defibrillator to a defibrillator electrode interface or connector 260 on the back frame. Those in turn can power the ECC device built in electrodes. In the embodiment illustrated, an electrical cable 266 may be seen extending from defibrillator 254 to ECC device 252.

Figure 9:
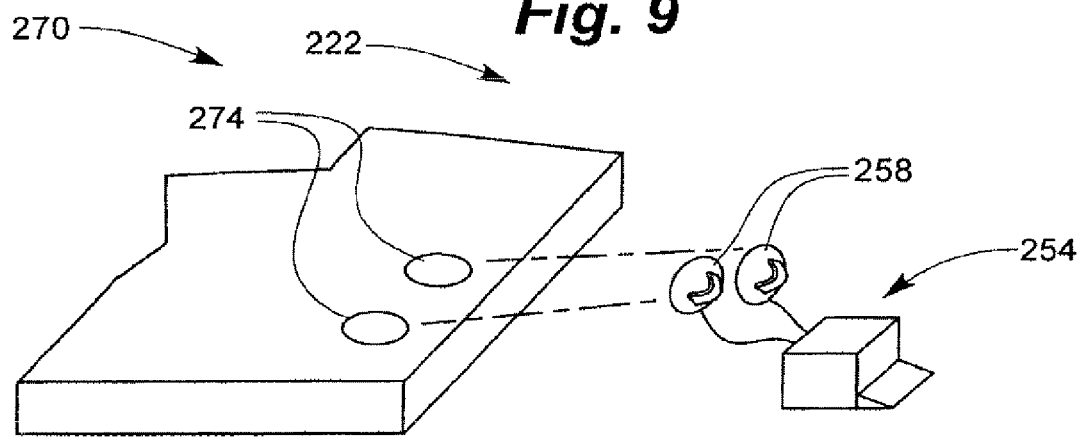

Referring to FIG. 9, an optional embodiment is shown. In the system 270, an FCC device 222 includes two electrodes 274 on the back frame for placing thereon directly the defibrillator electrodes 258. This way, no special wires are needed.

FIGS. 10 and 11 illustrate how defibrillator electrodes or other electrodes might be attached to an underside of the vest or belt of the chest compression portion of the devices of FIG. 1, 2, or 3. For example, the electrodes can be part of a belt or vest of FIG. 4 or 5. The electrodes can also be integrated with an arm or a prong of a chest compression member, for example, prong 208 of FIG. 6 or chest contact pad 235 or FIG. 7.

FIG. 10 illustrates a belt or vest having a first portion 300 coupled through a buckle or zipper 304 to a second portion 302. A first electrode 306 may be affixed to the underside of the belt or vest and coupled to a wire or lead 308. In FIG. 10, one of the electrodes is situated on the underside of the belt or vest, while the other electrode may be expected to be in the backboard. At least one wire can connect the electrode to the remainder of the defibrillation/pacing portion. This is a preferred embodiment, since it would minimize CPR artifact in the ECG signal. The electrode preferably avoids the center of the chest. That is where the buckle or zipper is shown (as wider than the open portion that supports the electrode).

FIG. 11 illustrates the belt or vest of FIG. 10, having belt or vest first portion 300, buckle or zipper 304, and second portion 302. First electrode 306 and wire 308 are as previously described with respect to FIG. 10. In FIG. 1, a second electrode 310 is coupled to a second wire or lead 312. In the embodiment illustrated in FIG. 11, no electrode is needed in the backboard or back frame for traditional defibrillation. At least one wire can connect each electrode to the defibrillation/pacing portion.

FIG. 12 illustrates the underside of another belt or vest having a first portion 320 coupled through a buckle or zipper 324 to a second portion 322. Belt or vest first portion 320 may be seen carrying a first electrode 326 and a second electrode 37, coupled to wires 332. Belt or vest second portion 322 may be seen carrying third electrode 328, fourth electrode 329, and fifth electrode 330, all coupled to wires 332. Wires 332, while having similar reference numbers, are, of course, preferably electrically distinct. The ECG leads of FIG. 12 are also preferably integrated with the underside of the vest or belt of the chest compression portion of the devices of FIG. 1, 2, or 3. The ECG leads may be placed so as to not interfere with any defibrillation electrodes, for example, those of FIGS. 10 and 11.

FIG. 13 illustrates yet another belt or vest having a first portion 340 coupled through a buckle or zipper 344 to a second portion 342. The underside of belt or vest first portion 340 may be seen carrying a first sensor 346 coupled to a wire or other signal transmission medium 349. The underside of belt or vest second portion 342 may be seen carrying a second sensor 347, and a third sensor 348, coupled to wires 349. The sensors are preferably also integrated with the underside of the vest or belt of the chest compression portion of the devices of FIGS. 1, 2 and 3. These sensors can include pulse detection sensors such as those made from piezoelectric materials, temperature sensors, $CO_2$ sensors, and other sensors for measuring physiological attributes or signals, well known to those skilled in the art.

The features integrated with the belt or vest are preferably arranged so that they do not interfere with each other. The electrode may be fully integrated, or detachable for servicing. Alternately and equivalently, some electrodes, ECG leads, or sensors may be hosted in the backboard.

FIGS. 14 and 15 illustrate how defibrillator electrodes, ECG leads, or sensors may be integrated with an underside of the vest, belt, or other chest compression members, for example those in FIG. 1, 2 or 3.

FIG. 14 illustrates a belt or vest 350 carrying an electrode, lead, or sensor 352. Electrode, lead, or sensor 352 can be coupled to a wire 356 and biased downward from the belt or vest with a spring 354, so as to be pressed against the chest of the patient. For use with a pulse sensor, some quieting time for the spring is preferably allowed, so as to not provide interference with the signal.

FIG. 15 illustrates a belt or vest 360 carrying an electrode, lead, or sensor 362 on the underside of the vest or belt. A gel or electrolyte 364 may be seen on the underside of the electrode, lead, or sensor 362. For implementing an electrode, a gel may be administered, or an electrolyte may be diffused. The gel or electrolyte may be provided in a capsule that bursts at an appropriate time to release it. The time may be prior to defibrillation electrotherapy. Bursting may be caused by the mere pressure against the chest, or by an appropriate electrical signal. One advantage that can be provided by some embodiments is that there is no need to disrobe the patient—the fluid may seep through the clothes to establish electrical conduction.

FIG. 16 illustrates some other optional features of the invention. ECC device 30, patient 100, and backboard 32 are shown, as previously described. A camera 382 may be seen disposed on a post secured to backboard 32. Camera 382 can be coupled to a communication module 380 that can act as a transmitter or transceiver. Communication module 380 can communicate with a remote assistance center 396 coupled through a network 394 and a remote antenna 392. A data/voice/video communications link 386 is shown as existing between communication module 380 and remote assistance center antenna 392. Communication link 386 can be bi-directional in some embodiments.

A data/voice/video communications link 390 is shown as existing between communication module 380 and defibrillation device communication module 384. Yet another communication link 388 may be seen between defibrillation device communication module 384 and remote assistance center antenna 392. Communication links 390 and 388 are also preferably bi-directional. In a preferred embodiment, communications modules 380 and/or 384 include the functionality of a portable telephone and can establish wireless communication with remote antenna 392, and network 394 is a network that can support voice and/or data communications.

Camera 382 is preferably a digital camera, and may be either a video camera or a still camera. A camera may be advantageously attached to a post in the backboard and/or to the defibrillation device. The camera is preferably attached to the ECC device. The camera permits recording of the scene and the patient. The recording may be used for record keeping, event analysis, and other purposes. Alternately, the recording may be used for live transmission to the remote assistance center 396, where more trained medical personnel can in turn provide feedback.

The user may use the defibrillator of the invention and/or the chest compression device of the invention to assist a victim. In addition, the user can establish a communication link 386 and/or 388 with remote assistance center 396. Then the information can be transmitted and can include images, if a camera is provided. The patient's vital signs, encoded by the invention for communication, along with the rescuer's comments, observations, and even questions may be also transmitted to the remote assistance center.

If the defibrillator of the invention and the chest compression device of the invention are interfaced, then only one communication link need be established with the Remote Assistance Center. The inputs from the other device can be passed via the interface.

In some embodiments, the invention is operable from remote assistance center 396. An operator at the remove assistance center can transmit a command code through communication link 392 to ECC device 30 and to the defibrillation device, and the devices operated accordingly. Such operation may actually include defibrillation and/or ECC.

Moreover, the monitored data, included also recorded data such as events, wave forms, physiological signals or attributes, and data indicative of the device operation itself may be also transmitted to a system for collecting or storing patient information, and to a computer-aided dispatch system for assistance. Furthermore, it may also be sent to a billing system for determining patient billing.

FIGS. 17 and 18 illustrate additional optional cooling figures of the invention. Cooling can be provided for performing IMHT (Induction of Mild Hypo Thermia), which may slow down adverse effects of the events being experienced by the patient.

ECC device 30 and patient 100 are as previously described. FIG. 17 illustrates generally a cooling module aspect of the present invention. In the example illustrated, the cooling module includes a liquid gas storage container or tank 402 coupled to a valve 404 coupled in turn to a tube 406 coupled to a cooling garment 408. Liquid gas storage container 402 can be included within the cooling module and is preferably carried under the backboard. This is most advantageous in the event the backboard is implemented with wheels.

The liquid in container 402 can be one that preferably turns into gas upon being released into the atmosphere. A cooling garment, similar to cooling garment 408, can be provided for each part of the body that is of interest to cool. As used herein, "cooling garments" include very loose, tent-type cooling garments that allow cool air to be blown over the patient. As used herein, "cooling garments" also include tightly adhering garments that may contact the patient's skin or clothing and conduct heat away through conductive cooling. Some tightly adhering cooling garments are adhesively adhered to the patient's skin and conduct heat away through a thermally conductive coupling agent. The cooling garment can be shaped to be suitable for placing over the bodily part that is to be cooled. Cooling garment 408 illustrated in FIG. 17 is designed for placement on the patient's head. Cooling may also be accomplished by evaporative cooling, for example, using a suitable fluid delivery system and an absorber for alcohol, such as cotton.

FIG. 18 illustrates a section of cooling garment 408. Garment 408 has an inner shell 409 for contacting patient 100. Garment 408 also has an outer garment or shell 411 that defines an inner space 405 between outer shell 411 and inner shell 409. Spacers may be used to maintain inner space 405 in an open configuration. Alternately, small tubes may be used. Garment 408 can receive liquid gas from storage container 402 via tube 406 in communication with inner space 405. The cooling gas or liquid can also be received into the series of small tubes, previously described. The gas can then be released into the atmosphere from various places in the garment. As it is being released, the gas can expand, cool, and thus draw heat away from the patient. Sensors, for example for temperature, may also be included.

Referring again to FIG. 17, the gas can be directed from storage container 402 to liquid controller or valve 404, and from there to garment 408 via tube 406. Liquid controller 404 can in turn be controlled by an IMHT controller, for controlling the rate of cooling of the patient. The expanded cooled gas may be mixed with air to control the final cooling gas/air temperature. The IMHT controller may be implemented in combination with the liquid controller, and optionally further communicates with the processor or controller of the device of the invention.

In some embodiments (e.g. FIG. 2) the interface is physical, and the devices are physically coupled to each other. In direct coupling embodiments, the external defibrillator may slide into a sheath of the back frame, and snap in place, making the required contacts. In other embodiments, the external defibrillator is coupled with the back frame via one or more wires. A physical interface is necessary if a defibrillation shock is to be transmitted, as in FIG. 8.

In other embodiments (e.g. FIG. 3) the interface is wireless, and the devices communicate without contacting each other. In that case, the defibrillator electrodes are applied directly to the patient. Allowance must be made for not interfering with the ECC device.

If the interface is wireless, it may use any one of many known technologies and protocols for wireless communication. Favored technologies are those that permit communication between devices that are within 10 m (30 feet) from each other, such as 802.11 compatible devices, Bluetooth devices, etc.

The interface can be established in many different ways. In the most advanced embodiments, both devices may exchange data with each other, and either may exercise control of the other. In other embodiments, either one of the devices of the invention may communicate to the other, but be able to receive no commands. Or they may be able to receive commands, but not communicate to the other.

The exchanged data includes device data such as identification, settings, status, time stamps, etc. The exchanged data may also include user inputs, patient physiologic parameters, electrotherapy, etc. The control data may include the ability of one device to control the state of the other; to recognize and interpret the inputs of the other for making decisions. In addition, there can be "analog" connection to therapy electrodes, ECG electrodes, or other sensors.

The handshake may be established with the one device as "master" and the other as "slave", or both as peers. A peer connection is not favored, since that might require a user to be operating two I/O modules. In addition, prompts in at least one of the devices might assist the user in connecting the device to the other.

The determination of which one should be master is preferably made by comparing their relative capability to coordinate the devices. Such may start even wirelessly, as they are brought close to each other. An example is described below.

FIG. 19 is a view of a sample screen 500 of a defibrillator according to the invention, when it requests connection with an ECC device according to the invention. The device ID may be seen at 502. Remarks can be displayed at 504. The detection of a cooperating device is noted at 506. The coordination capability of the coordinating device is displayed at 508. A master-slave relationship is initiated at 510.

FIG. 20 is a view of a sample screen 520 of the ECC, when the request is received. The device ID may be seen at 522. Remarks are displayed at 524. The detection or a cooperating device is noted at 526. Receipt of request for a master-slave relationship is displayed at 528. The use is prompted for acceptance of the master-slave relationship at 530.

The device that is in control preferably takes over all input/output functionality. In addition, it takes control of operations of both devices under a single operation.

As the connection is established, compatibility is determined of the various functions, inputs, etc. An example is seen below.

Referring to FIG. 21, a screen 550 is shown of when compatibility is established at 558. The clocks are synchronized at 556. This may take place by coordinating the time stamps of the two devices, either by using a common clock, or by communication of events, or by denoting a difference between the times shown by the clocks of the devices. Various inputs are checked at 558, to see if they will be understood if received.

The present invention may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented as an Application Specific Integrated Circuit (ASIC), etc. These features can be integrated with the invention, or coupled with it.

Moreover, the invention additionally provides methods, which are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between the method of the invention itself and the method of operating a computing machine. The present invention relates both to methods in general, and also to steps for operating a computer and for processing electrical or other physical signals to generate other desired physical signals.

The invention additionally provides programs, and methods of operation of the programs. A program is generally defined as a group of steps leading to a desired result, due to their nature and their sequence. A program made according to an embodiment of the invention is most advantageously implemented as a program for a computing machine, such as a general-purpose computer, a special purpose computer, a microprocessor, etc.

The invention also provides storage media that, individually or in combination with others, have stored thereon instructions of a program made according to the invention. A storage medium according to the invention is a computer-readable medium, such as a memory, and is read by the computing machine mentioned above.

The steps or instructions of a program made according to an embodiment of the invention requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

FIG. 22 illustrates a general computer, processor, or controller 440 having a data storage device or computer readable medium 446 interfaced with computer 440 to transfer data via link 448, or the data may define a program. Computer 440 of FIG. 22 may be implemented by a CPU, and preferably interfaces with either one of the 10 modules or human interface devices previously described. Computer or controller 440 includes a memory 442 containing executable logic or program 444.

This detailed description is presented largely in terms of flowcharts, display images, algorithms, and symbolic representations of operations of data bits within at least one computer readable medium, such as a memory. An economy is achieved in the present document in that a single set of flowcharts is used to describe both methods of the invention, and programs according to the invention. Indeed, such descriptions and representations are the type of convenient labels used by those skilled in programming and or the data processing arts to effectively convey the substance of their work to others skilled in the art. A person skilled in the art of programming may use these descriptions to readily generate specific instructions for implementing a program according to the present invention.

Often, for the sake of convenience only, it is preferred to implement and describe a program as various interconnected distinct software modules or features, individually and collectively also known as software and softwares. This is not necessary, however, and there may be cases where modules are equivalently aggregated into a single program with unclear boundaries. In any event, the software modules or features of the present invention may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps which may be performed by different modules of an overall parts of a software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

In the present case, methods of the invention are implemented by machine operations. In other words, embodiments of programs of the invention are made such that they perform methods of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

Methods of the invention are now described.

Referring now to FIG. 23, a flowchart 2000 is used to illustrate a method according to an embodiment of the invention. The method of flowchart 2000 may also be practiced by the devices of the invention described in this document. Above and beyond the method described herein, the responder (who is also a user) may be instructed on how to apply a device, and or interactively give feedback, and/or to perform steps of the method, etc.

According to a box 2010, signals are received about the patient, and optionally are also monitored. Optionally, they are also recorded, displayed, transmitted, etc.

The signals are received from the patient (such as ECG), from special sensors (such as oximetry, impedance, force, pulse detection sensors, etc.). Signals may also be received from other components or devices (size of belt or vest around patient's chest, GPS signals, control signals from a device of a responder attending to the patient, etc.). Signals may further be received from the responder interactively, e.g. by asking questions and receiving answers.

The signals are then analyzed and treated as inputs, as is also shown in the rest of flowchart 2000. Analysis may be implemented also by taking advantage of the combined functionalities and features. For example, knowledge of the time profile of the chest compression is used to remove the chest compression artifact from the ECG.

The process of box 2010 preferably takes place continuously, even if execution moves also to other boxes of flowchart 2000, Monitoring is for the conditions that are applicable for the below, including, for example, for the effectiveness of chest compressions. There can be different stages of monitoring, such as main monitoring, at exact box 2010, and secondary monitoring concurrent with other stages, e.g. at the same time as any one of boxes 2030, 2040, 2080 below.

In addition, monitoring may be also for detecting Acute Myocardial Infarction (AMI), via the ECG or other monitoring parameters, and indicating this to the caregiver. If AMI is detected, then monitoring may also be for cardiac arrest (which commonly occurs during an AMI).

In addition to monitoring, preferably there is also recording. The accumulated record may include records of events, data monitored, and functionalities of the invention that are operating, and time profiles of their operation.

A number of decision trees may then be implemented, in determining what action to take next. The best embodiments known to the inventors are described, but that is only by way of example, and not of limitation. Further, the flowchart may be integrated with other steps, such as administering medications (e.g. cardiac drugs), etc. But simplistically, the ECC input is analyzed for a shockable rhythm, and then either defibrillation takes place, or pulse or other signs of circulation are checked, following the same protocol as today's AEDs. Further, a user would be prompted to start the chest compression device and ventilations if there was no pulse (or no signs of circulation.) A more rigorous way is described below.

According to a next box 2020, it is determined whether Ventricular Fibrillation (VF) of the patient's heart is occurring. If so, then according to a next box 2030, the patient is defibrillated. This is accomplished by administering electrotherapy, such as a defibrillation shock. If a child ("pediatric") patient is sensed, then the defibrillation energy level may be adapted automatically (e.g. be set to 50 J). Such sensing may be from responder inputs, the belt or vest size when tightened around the patient, etc.

In some embodiments of the invention, at box 2030, instead of delivering a defibrillation shock, the CPR portion is used to deliver a precordial thump to deliver the patient. In particular, when the device detects a shockable rhythm, rather than delivering an electrical defibrillation pulse, the device first deliver a precordial thump to the patient, via the chest compression device, to attempt defibrillation. This is a great advantage of the invention, in that it can revert from one form of therapy to another.

In yet other embodiments, based on the patients downtime (which could be entered into the device by the caregiver), or by analysis of parameter that indicates probability of shock success (such as ECG), it may first be decided whether to deliver electrotherapy, or to first perform CPR, and/or to first deliver medications prior to defibrillating. That action could either be started automatically by the system, or could be started with manual action from the user.

Execution may then return to box 2010, where inputs are received and analyzed. In a preferred optional embodiment, however, according to a next box 2040, Cardiopulmonary Resuscitation (CPR) is either performed automatically, or instructed for the responder to perform, after defibrillating. Instruction may be by voice commands, and/or may include sounds for the responder to synchronize their action. In addition, depending on the monitored inputs, the repetition rate of the CPR is adjusted. Further, if CPR is performed automatically, the force and its time profile are also adjusted. Execution returns to box 2010.

According to important alternate embodiments of the invention, boxes 2030 and 2040 take place together. In other words, defibrillation takes place while CPR is being performed automatically.

Referring briefly to FIG. 24, a time profile of the chest compressions is shown. More particularly, the changing circumference of the patient chest is plotted, as squeezed and released. In addition, the level of patient impedance is plotted in dashed lines, following in pattern the time profile of the chest circumference. (Other impedance variations may be superimposed on the level of impedance). The profile of chest squeezing may be known directly, or indirectly from a monitored parameter such as the level of impedance.

Advantageously, defibrillation (the large lightning bolts in FIG. 24) may take place any time in the CPR cycle. The exact timing is chosen in synchronization to pursue various optimizations. For example, if it is desired to exploit the smallest possible impedance, defibrillation happens according to bolt (A). On the other hand, if it is desired to exploit the moment that the heart is filled with the most blood (and thus draw the most current through the heart), then defibrillation happens according to bolt (B).

CPR may continue after defibrillation, or even be halted after it. An advantage of the invention is that the waiting time from CPR to defibrillation is minimized. Pacing takes place as described later in this document.

Returning to FIG. 23, if, at box 2020 it is determined that the patient is not undergoing VF, then according to an optional next box 2050, it is inquired whether a pulse is detected. If not, then according to an optional next box 2060, it is inquired whether the condition of Ventricular Tachycardia (VT) is detected. If so, then execution reverts to box 2030, and the patient is defibrillated. But if no VT is detected at box 2060, then execution reverts to box 2040 for performing CPR.

If a pulse is detected at box 2050, then, according to an optional next box 2070, it is inquired whether respiration is detected. If so, then execution returns to box 2010. Respiration may be detected automatically by respiration sensors, such as a $CO_2$ (carbon dioxide) sensor, chest movement sensor, or an impedance sensor.

If at box 2070 there is no respiration detected, then according to an optional next box 2080, ventilation is performed automatically by a ventilator, or rescue breathing is instructed for the responder to perform. Execution returns to box 2010.

Since box 2010 is preferably executed continuously, the method also includes discontinuing one type of therapy, and optionally also starting another consistently with the above. Also, if one of the signs changes, execution may return to box 2010 and start over. For example, pulse may be lost while ventilating. Or the onset of respiration may be detected, in which case other activities (such as ventilation) stop.

Referring now to optional box 2090, optional pacing according to the invention is also described. In the embodiment of FIG. 23, the condition for enabling pacing is examined in two circumstances, namely in transitioning from box 2050 to 2070, and also in transitioning from box 2060 to 2040.

Referring now to FIG. 25, box 2090 is described in more detail. In both cases, it is inquired whether severe bradycardia is detected. In addition, if no pulse has been detected, it is inquired whether ventricular asystole has been detected. If not, then execution continues as before (from box 2050 to 2070, and from box 2060 to 2040). If yes, then according to a box 2095, pacing is performed.

Returning to FIG. 24, pacing (shown as a small lightning bolt) may also be coordinated with the administration of CPR. Pacing is preferably synchronized with the compression cycle. There is some evidence that chest compressions may cause a QRS complex (ventricular depolarization), if the heart is able to support it. Accordingly, pacing during the compression cycle provides the additional impetus to the ventricles. Also, pacing should be avoided a few 100 msec after a QRS complex, during the ventricular vulnerability period.

At any one time during the method of FIG. 23, inputs are received (for monitoring) from the available sensors, from the user through the I/O module, and from the interfaces during communication. Outputs are communicated to the user through the I/O module, sometimes through the interface during implementation.

Referring now to FIG. 26, a sample screen is shown for communicating to the user the outputs. In the example of FIG. 21, there is a count down for imminent defibrillation (at the 3 sec point). The screen is preferably from the "master" device in the relationship. Some of the inputs are generated on board, while others are generated by the other device, and received by the interface.

A person skilled in the art will be able to practice the present invention in view of the description present in this document, which is to be taken as a whole. Numerous details have been set forth in order to provide a more thorough understanding of the invention. In other instances, well-known features have not been described in detail in order not to obscure unnecessarily the invention.

While the invention has been disclosed in its preferred form, the specific embodiments as disclosed and illustrated herein are not to be considered in a limiting sense. Indeed, it should be readily apparent to those skilled in the art in view of the present description that the invention may be modified in numerous ways. The inventors regard the subject matter of the invention to include all combinations and sub combinations of the various elements, features, functions and/or properties disclosed herein.

What is claimed is:

1. A system comprising:
    an external chest compression device having a first communication module and a first controller, wherein the first controller is operably coupled to the external chest compression device and the first communication module;
    a defibrillator having a second communication module and a second controller, wherein the second controller is operably coupled to the defibrillator and the second communication module; and
    at least one sensor configured to sense data indicative of blood perfusion and coupled to at least one of the first controller and the second controller,
    wherein at least one of the first controller and the second controller is configured to analyze the sensor data to monitor blood perfusion over time and to generate an output responsive to the monitored blood perfusion to change a characteristic of chest compression being delivered with the external chest compression device, and
    wherein the first communication module and the second communication module are configured for wireless communication therebetween and form a wireless interface between the external chest compression device and the defibrillator.

2. A system as in claim 1 wherein the external chest compression device includes the at least one sensor.

3. A system as in claim 2 wherein the first communication module of the external chest compression device is coupled to the at least one sensor.

4. A system as in claim 2 wherein the at least one sensor configured to sense data comprises at least one sensor configured to sense at least one attribute from the group consisting of pulse, heartbeat, breathing, body temperature, externally applied chest pressure and thoracic impedance.

5. A system as in claim 1 wherein the external chest compression device includes a chest compression member, the chest compression member including at least one pressure sensor disposed thereon and coupled to the first communication module.

6. A system as in claim 1 wherein the external chest compression device includes a manually operable chest compression member.

7. A system as in claim 1 wherein the external chest compression device includes a backboard and a ventilator operably coupled to the backboard.

8. A system as in claim 7 wherein the ventilator is coupled to the first communication module.

9. A system as in claim 1 wherein the first communication module and the second communication module utilize a wireless communications protocol selected from the group consisting of Bluetooth and 802.11.

10. A system as in claim 1 wherein the first communication module and the second communication module utilize a wireless communications medium selected from the group consisting of radio frequency and infrared light.

11. A system as in claim 1 wherein at least one of the first controller and the second controller is configured to execute logic for coordinating external chest compression and defibrillation based on data transmitted between the first communication module and the second communication module.

12. A system as in claim 1, further comprising:
a chest compression member,
an electrode disposed on the chest compression member,
a first electrical connector electrically coupled to the electrode disposed on the chest compression member,
in which the defibrillator includes a second electrical connector adapted to connect to the first electrical connector.

13. A system as in claim 1, in which at least one of the first controller and the second controller is configured to execute logic to monitor chest compressions over time and to generate an output to administer a defibrillation pulse in synchrony with chest compressions.

14. A system as in claim 1, wherein the at least one sensor comprises a sensor for monitoring ECG signals, and the sensor for monitoring ECG signals is coupled to at least one of the first and second controllers, in which the at least one of the first and second controllers executes logic to administer pacing after an ECG signal indicates that a defibrillation pulse results in a perfusing ECG rhythm.

15. A system as in claim 1, wherein the at least one sensor comprises a sensor for monitoring ECG signals, and the sensor for monitoring ECG signals is coupled to at least one of the first and second controllers, in which the at least one of the first and second controllers executes logic to administer external chest compression after an ECG signal indicates that a defibrillation pulse has not resulted in a perfusing ECG rhythm.

16. A system as in claim 1, further comprising a cooling module.

17. A system as in claim 16 wherein the cooling module includes a cooling garment.

18. A system as in claim 16, wherein at least one of the first controller and the second controller is configured to execute logic in response to sensor data indicative of cardiac arrest to initiate cooling using the cooling module.

19. A system as in claim 1, wherein the external chest compression device includes an automatic chest compressions device, and the output to change a characteristic of chest compression includes an output that causes the external chest compression device to automatically adjust.

* * * * *

UNITED STATES PATENT AND TRADEMARK OFFICE
CERTIFICATE OF CORRECTION

PATENT NO. : 8,121,681 B2
APPLICATION NO. : 11/953665
DATED : February 21, 2012
INVENTOR(S) : David R. Hampton et al.

Page 1 of 1

It is certified that error appears in the above-identified patent and that said Letters Patent is hereby corrected as shown below:

Column 1, line 11 should read "587, filed Feb. 14, 2003, titled COOPERATING DEFIBRIL-"
Column 1, line 19 should read "DEFIBRILLATORS LEARNING OF OTHER CONCUR-"
Column 2, line 24 should read "ECG signals, EEG activity, thoracic impedance, and other"
Column 3, line 36 should read "to the sensors (e.g. pulse or ECG)."
Column 4, line 55 should read "ECG lead, or sensor;"
Column 6, line 58 should read "to FIG. 1. ECC device 120 includes a short backboard or back"
Column 8, line 22 should read "178. In yet another way, chest compression is effected by"
Column 8, line 30 should read "backboard 210. In the embodiment illustrated, arms 202 are"
Column 9, line 21 should read "the system 270, an ECC device 222 includes two electrodes"
Column 9, line 48 should read "described with respect to FIG. 10. In FIG. 11, a second elec-"
Column 9, line 58 should read "327, coupled to wires 332. Belt or vest second portion 322 may"
Column 13, line 14 should read "Remarks are displayed at 524. The detection of a cooperating"
Column 16, line 2 should read "tions (e.g. cardiac drugs), etc. But simplistically, the ECG"
Column 16, line 27 should read "In yet other embodiments, based on the patient's downtime"

Signed and Sealed this
Twenty-ninth Day of January, 2013

David J. Kappos
*Director of the United States Patent and Trademark Office*